United States Patent
Seto

(10) Patent No.: US 9,588,043 B2
(45) Date of Patent: Mar. 7, 2017

(54) MEASUREMENT APPARATUS AND MEASUREMENT METHOD

(71) Applicant: CANON KABUSHIKI KAISHA, Tokyo (JP)

(72) Inventor: Takamasa Seto, Ebina (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/635,044

(22) Filed: Mar. 2, 2015

(65) Prior Publication Data

US 2015/0260647 A1    Sep. 17, 2015

(30) Foreign Application Priority Data

Mar. 12, 2014  (JP) ................. 2014-049314

(51) Int. Cl.
  *G01N 21/47*  (2006.01)
  *G01N 21/55*  (2014.01)

(52) U.S. Cl.
  CPC .......... *G01N 21/55* (2013.01); *G01N 21/4738* (2013.01); *G01N 2021/4711* (2013.01)

(58) Field of Classification Search
  CPC .................. G01N 21/47; G01N 21/55; G01N 2021/4711; G01N 2201/125
  USPC ..... 356/445–446, 237.2, 420, 601, 625, 368
  See application file for complete search history.

(56) References Cited

U.S. PATENT DOCUMENTS

| | | | | |
|---|---|---|---|---|
| 5,289,260 A * | 2/1994 | Miyazaki | ................ | G06K 9/74 356/237.5 |
| 6,172,373 B1 * | 1/2001 | Hara | ...................... | G03F 7/707 250/548 |
| 6,975,404 B2 * | 12/2005 | Schwarz | ............... | G01N 21/474 356/446 |
| 7,852,481 B2 * | 12/2010 | Imura | ..................... | G01N 21/57 250/548 |
| 7,859,659 B2 * | 12/2010 | Xu | ...................... | G01B 11/0641 356/300 |
| 2002/0018210 A1 * | 2/2002 | Maris | ..................... | G01B 11/02 356/432 |
| 2007/0139659 A1 * | 6/2007 | Hwang | ................ | G01B 11/002 356/614 |
| 2007/0195327 A1 * | 8/2007 | Okui | ...................... | G01N 21/57 356/445 |
| 2007/0258093 A1 * | 11/2007 | Sieck | ..................... | G01N 21/55 356/446 |
| 2007/0273886 A1 * | 11/2007 | Matsumoto | ............ | G01N 21/57 356/446 |
| 2012/0099089 A1 * | 4/2012 | Sogard | ..................... | G03F 1/84 355/52 |

(Continued)

FOREIGN PATENT DOCUMENTS

JP    2006-275955 A    10/2006

*Primary Examiner* — Tarifur Chowdhury
*Assistant Examiner* — Isiaka Akanbi
(74) *Attorney, Agent, or Firm* — Fitzpatrick, Cella, Harper & Scinto

(57) ABSTRACT

A sensor unit photoelectrically converts received light to output image data. A lens unit condenses light reflected by an object surface to be measured on the sensor unit. A lens control unit controls a geometric condition of rays passing through the lens unit. The sensor unit and the lens control unit are controlled to acquire a multi-angular reflectance property in a neighborhood of a specular reflection direction of the object surface.

14 Claims, 16 Drawing Sheets

(56) References Cited

U.S. PATENT DOCUMENTS

2014/0152990 A1\* 6/2014 Ehbets ..................... G01J 3/50
356/405

\* cited by examiner

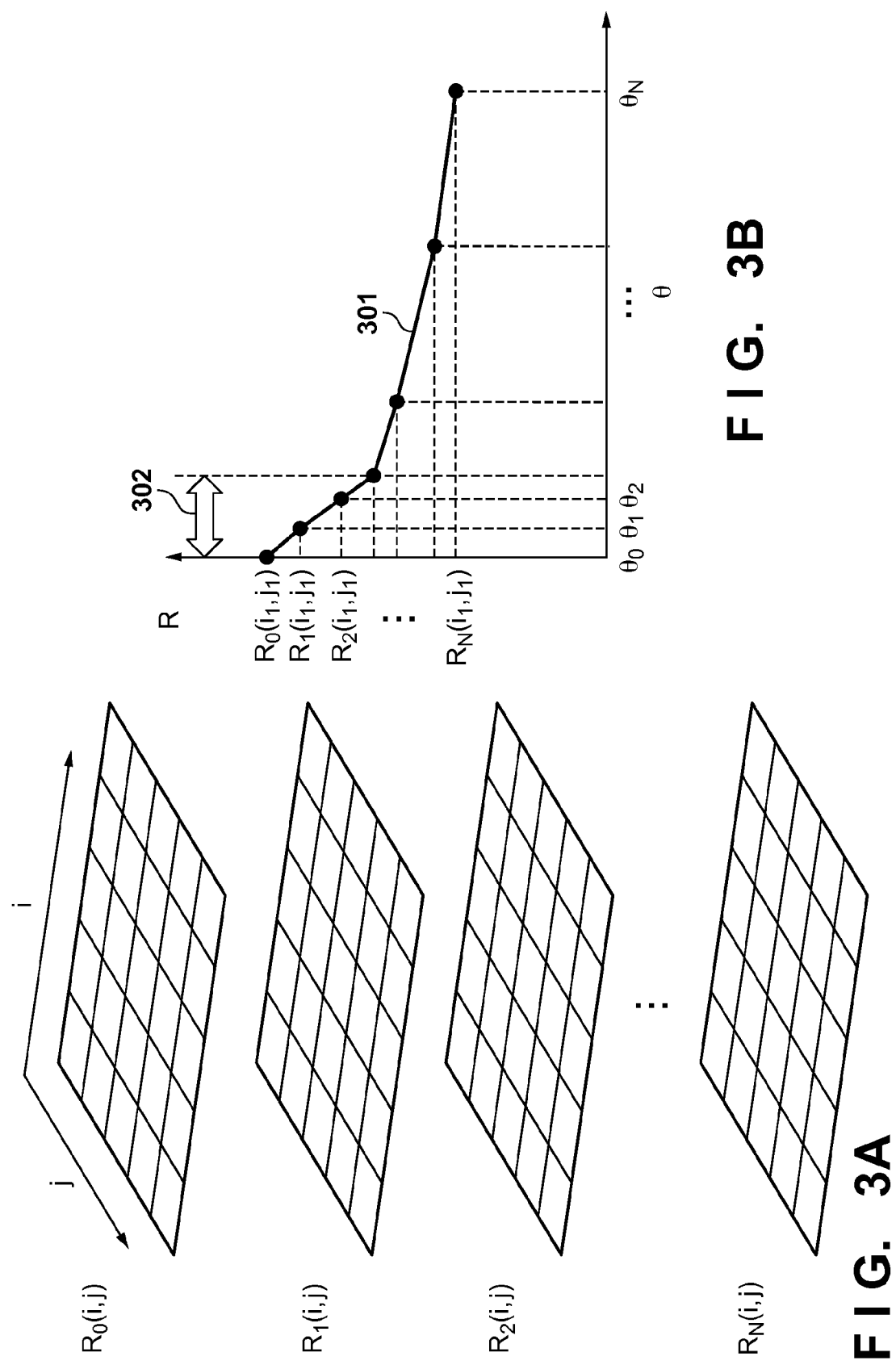

MEASUREMENT APPARATUS AND MEASUREMENT METHOD

BACKGROUND OF THE INVENTION

Field of the Invention

The present invention relates to acquisition of the multi-angular reflectance property of an object surface.

Description of the Related Art

A goniophotometer is known as a measurement apparatus that acquires a multi-angular reflectance property as the multi-angular property of the reflectance on an object surface. Japanese Patent Laid-Open No. 2006-275955 (literature 1) discloses a measurement apparatus that switches the irradiation direction of light with respect to an object to irradiate the object with light, and also switches the capturing direction, with respect to the object, of a camera configured to capture the object placed on a table. The measurement apparatus disclosed in literature 1 can acquire the two-dimensional distribution of the multi-angular reflectance property of an object. Such a measurement apparatus acquires a multi-angular reflectance property by changing geometric conditions such as the irradiation direction of light and the capturing direction.

However, the reflectance of a metal or the like in the neighborhood of the specular reflection direction greatly varies by even a small difference of the angle. For example, the above-mentioned measurement apparatus takes a long time for measurement because measurement is repeated while changing geometric conditions at a small step such as a 0.2 degree step in the neighborhood of the specular reflection direction. Since geometric conditions need to be changed at high accuracy, a device such as a multi-angle stage configured to change the angle of a placed object becomes expensive.

SUMMARY OF THE INVENTION

In one aspect, a measurement apparatus comprises: a sensor unit configured to photoelectrically convert received light to output image data; a lens unit configured to condense light reflected by an object surface to be measured on the sensor unit; a lens control unit configured to control a geometric condition of rays passing through the lens unit; and a measurement control unit configured to control the sensor unit and the lens control unit so as to acquire a multi-angular reflectance property in a neighborhood of a specular reflection direction of the object surface.

According to the aspect, the multi-angular reflectance property of an object surface in the neighborhood of the specular reflection direction can be measured more easily. In addition, the multi-angular reflectance property can be measured by a simple apparatus at high accuracy.

Further features of the present invention will become apparent from the following description of exemplary embodiments with reference to the attached drawings.

BRIEF DESCRIPTION OF THE DRAWINGS

FIGS. 2A, 2B, 3A, and 3B are views for explaining the multi-angular reflectance property.

DESCRIPTION OF THE EMBODIMENTS

Preferred embodiments of the present invention will now be described with reference to the accompanying drawings. Note that an arrangement described in the following embodiment is merely an example, and the present invention is not limited to the illustrated arrangement.

First Embodiment

[Apparatus Arrangement]

Figure 1:
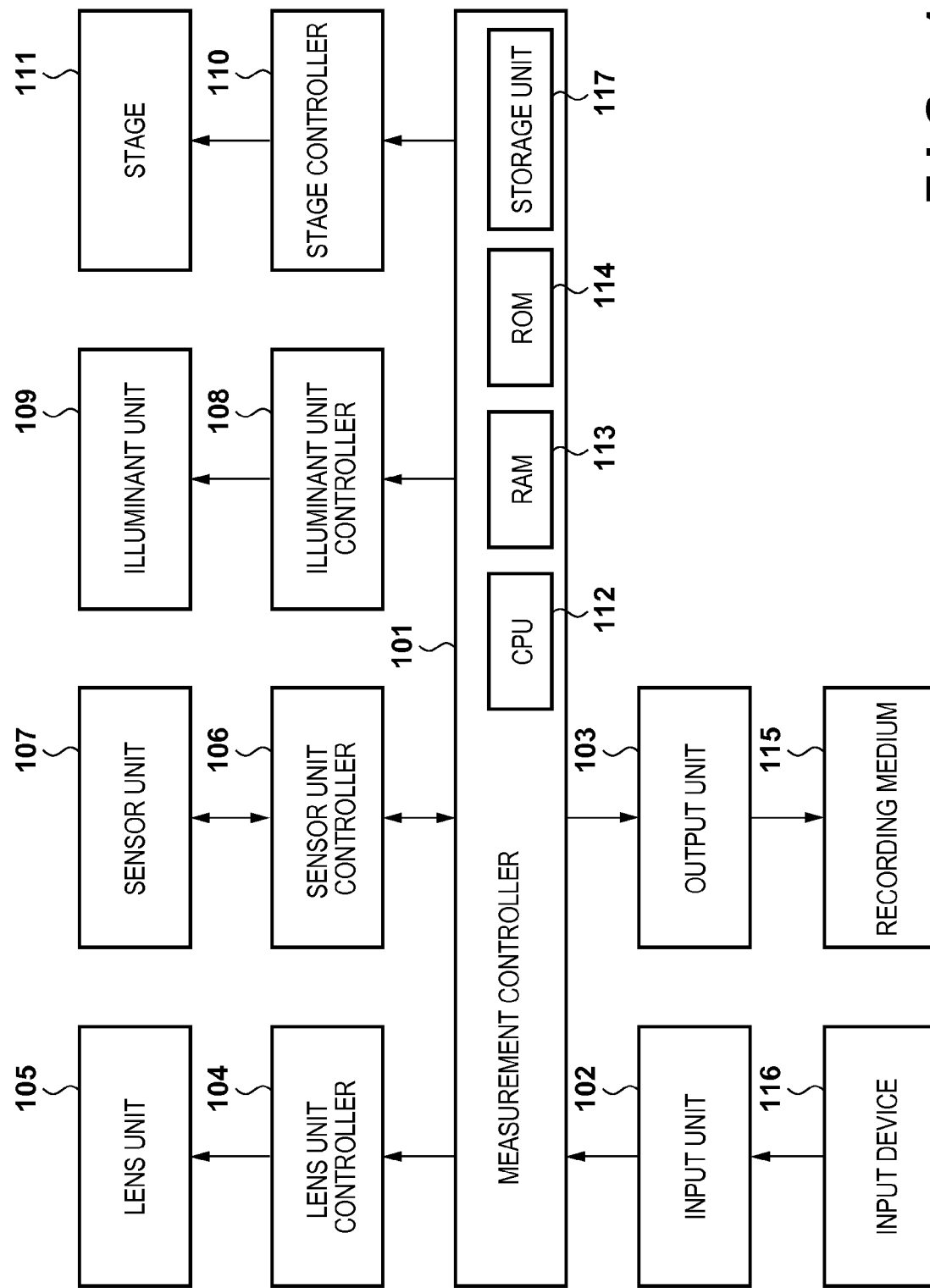
FIG. 1 is a block diagram showing the arrangement of a measurement apparatus according to an embodiment.

FIG. 1 is a block diagram showing the arrangement of a measurement apparatus according to the first embodiment. The measurement apparatus according to this embodiment acquires the multi-angular reflectance property of an object. In FIG. 1, a measurement controller 101 performs a series of control operations to send necessary control signals to a lens unit controller 104, a sensor unit controller 106, and an illuminant unit controller 108, and to output a multi-angular reflectance property from an output unit 103.

A microprocessor (CPU) 112 of the measurement controller 101 executes an operating system (OS) stored in a read only memory (ROM) 114. When a measurement start instruction is input from an input unit 102, the CPU 112 loads, to a random access memory (RAM) 113, a measurement program stored in advance in the ROM 114 or a storage unit 117 such as a hard disk drive (HDD), and executes the measurement program. Details of measurement processing implemented by the measurement program will be described later.

The input unit 102 receives a measurement start instruction or the like from an input device 116 such as a keyboard or a mouse. The output unit 103 records an acquired multi-angular reflectance property on a recording medium 115 such as a memory card.

Note that the input unit 102 and the output unit 103 are general-purpose interfaces such as a USB (Universal Serial Bus). The CPU 112 can store, in the storage unit 117 through the input unit 102, the measurement program stored in the recording medium 115, and can load the measurement program to the RAM 113.

A lens unit 105 condenses light reflected by an object to be measured. As the lens unit 105, an imaging lens that is telecentric in the space of an object to be measured is desirably used. The lens unit 105 includes a diaphragm 401 (to be described later). In this embodiment, the aperture angle of the lens unit 105 with respect to an object is controlled by changing the aperture of the diaphragm 401. In accordance with a command from the measurement controller 101, the lens unit controller 104 performs control to move the aperture blades of the diaphragm 401 or the like in the lens unit 105 and change the aperture.

Figure 13:
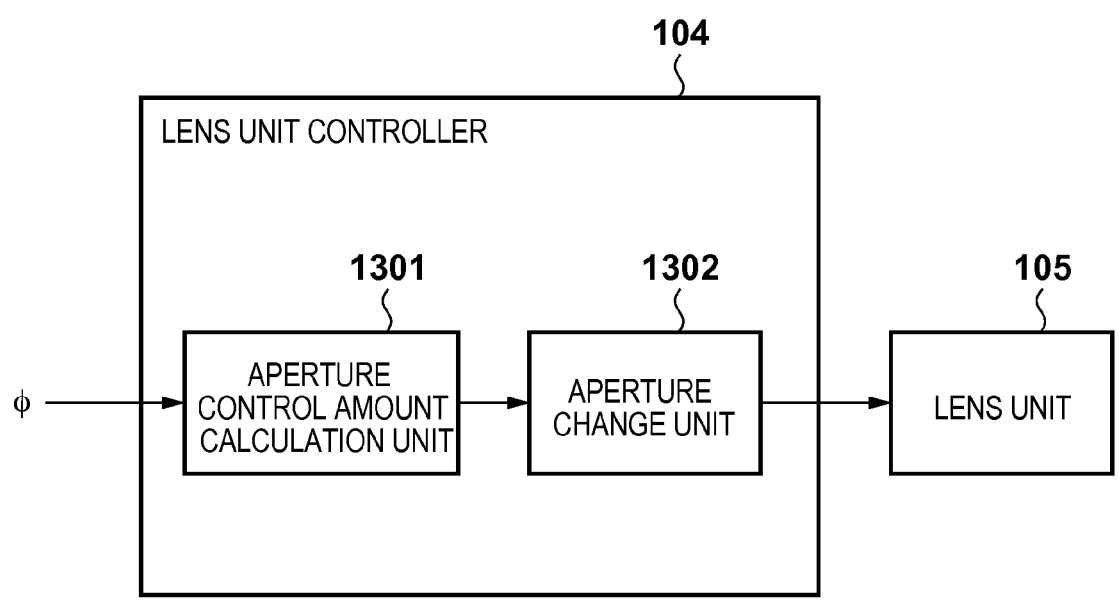
FIG. 13 is a block diagram showing the arrangement of a lens unit controller according to the first embodiment.

FIG. 13 is a block diagram showing the arrangement of the lens unit controller 104. When a value φ representing an aperture diameter is input from the measurement controller 101 to the lens unit controller 104, an aperture control amount calculation unit 1301 calculates mechanical control amounts such as aperture blade positions at which the aperture diameter of the diaphragm 401 becomes φ. Then, an aperture change unit 1302 drives the stepping motor (not shown) of the lens unit 105 or the like to move the aperture blades to the aperture blade positions calculated by the aperture control amount calculation unit 1301. Note that the present invention does not limit the shape, operation principle, and control method of the diaphragm 401, and it is only necessary to change the aperture diameter to the indicated value φ.

Referring back to FIG. 1, a sensor unit 107 senses light condensed by the lens unit 105. The sensor unit 107 is an area sensor in which charge coupled devices configured to photoelectrically convert light condensed by the lens unit 105, and light receiving elements such as CMOSs are two-dimensionally disposed. Each light receiving element is connected to an analog-to-digital converter (ADC) for every element or every plurality of elements. The sensor unit 107 outputs image sensing data representing the intensity of light received by each light receiving element. The sensor unit controller 106 performs processing of controlling image sensing processing of the sensor unit 107 in accordance with a command from the measurement controller 101, and sending, to the measurement controller 101, image sensing data output from the sensor unit 107.

This embodiment assumes, as the sensor unit 107, an area sensor in which light receiving elements are two-dimensionally disposed. This embodiment is premised on that each light receiving element of the area sensor has a linear photoelectric conversion characteristic, and the sensor unit 107 outputs a quantized signal having a linear characteristic with respect to the illuminance of light irradiating the light receiving surface of the area sensor. However, the present invention is not limited to this. For example, a camera which includes an image sensing device with a resolution of 1,024 pixels (vertical)×1,024 pixels (horizontal) and a size of ⅔ inches, and in which the significant bit depth of an output value is 10 bits can be used as the area sensor. Further, this embodiment assumes, as the sensor unit 107, a monochrome area sensor having a spectral sensitivity characteristic equivalent to a luminosity factor characteristic for simplicity. However, the sensor unit 107 is not limited to this example, and may be an RGB area sensor in which R, G, and B filters are disposed in a Bayer pattern on the light receiving surface, or a spectrum camera devised to have an arbitrary spectral sensitivity characteristic.

An illuminant unit 109 includes an illuminant such as a light emitting diode (LED) or a xenon lamp, and a collimator. Light emitted from the illuminant unit 109 to an object is desirably changed into parallel rays through the collimator or the like. The irradiation area is desirably an area wider than an image sensing range where the sensor unit 107 senses an image through the lens unit 105. The illuminant unit controller 108 controls the ON/OFF state of the illuminant, the light emission intensity, the irradiation area, and the like in accordance with commands from the measurement controller 101.

A stage 111 is a stage for controlling the relative positions of an object surface to be measured and the illuminant, and the relative positions of the object surface and the light receiving surface of the sensor unit 107. The stage 111 is a goniometer stage capable of multi-angle control. A stage controller 110 includes an actuator configured to control the relative positions in accordance with a command from the measurement controller 101, and move the stage 111 such that the illuminant and the object surface form an indicated angle, and the object surface and the light receiving surface form an indicated angle.

[Multi-Angular Reflectance Property]

Figure 2A:
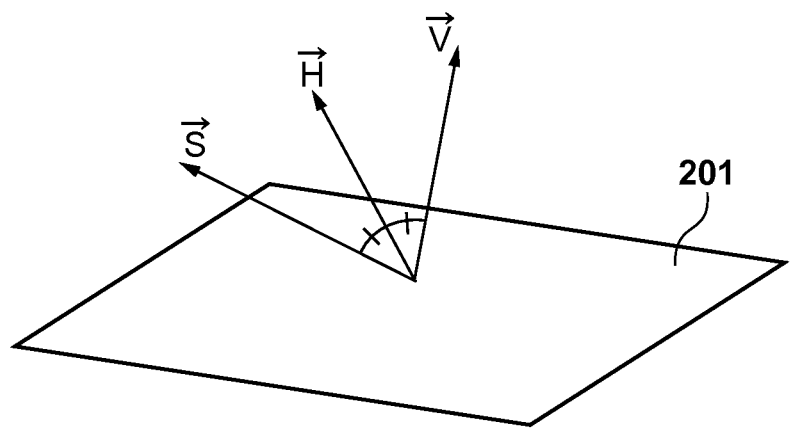

The multi-angular reflectance property that is measured by the measurement apparatus according to this embodiment will be explained with reference to FIGS. 2A, 2B, 3A, and 3B. In this embodiment, for example, a vector A is denoted as "$\vec{A}$". First, a half vector $\vec{H}$ will be explained with reference to FIG. 2A. In FIG. 2A, a light source vector $\vec{S}$ is a unit vector indicating the direction of the light source from a given point (to be referred to as a "measurement point" hereinafter) on the surface of an object 201 to be measured. A line-of-sight vector $\vec{V}$ is a unit vector indicating a direction in which the measurement point of the object 201 is observed. The half vector $\vec{H}$ is a vector indicating an intermediate direction between the light source vector $\vec{S}$ and the line-of-sight vector $\vec{V}$ and is given by:

$$\vec{H} = (\vec{S}+\vec{V})/|\vec{S}+\vec{V}| \qquad (1)$$

Figure 2B:
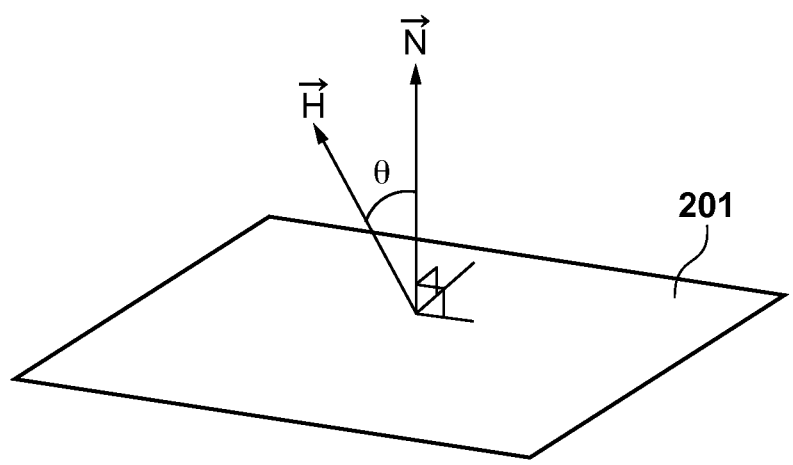

Next, the angle in the multi-angular property will be explained with reference to FIG. 2B. In FIG. 2B, the reflectance of the measurement point of the object 201 with respect to an angle θ formed by the normal vector $\vec{N}$ of the measurement point of the object 201 and the half vector $\vec{H}$ is measured as a multi-angular reflectance property. Note that θ shown in FIG. 2B will be called a "declination angle". The declination angle θ is calculated by:

$$\theta = \cos^{-1}\{(\vec{H}\cdot\vec{N})/(|\vec{H}||\vec{N}|)\} \qquad (2)$$

FIG. 3A is a view for explaining the structure of data measured by the measurement apparatus according to this embodiment. In FIG. 3A, $R_0(i, j)$ is the two-dimensional distribution (reflectance image) of reflectances measured at a given declination angle $\theta_0$, and has a spatial resolution corresponding to the number of pixels of image data obtained by the sensor unit 107 by capturing. Note that (i, j) are variables indicating vertical and horizontal coordinate positions in the two-dimensional distribution of measurement points. Similarly, $R_1(i, j)$ indicates the two-dimensional distribution of reflectances measured at a given declination angle $\theta_1$, and $R_2(i, j)$ indicates the two-dimensional distribution of reflectances measured at a given declination angle $\theta_2$. That is, two-dimensional distributions of reflectances exist by the number N+1 of declination angles θ used for measurement. The measurement apparatus according to this embodiment outputs N+1 two-dimensional distributions of reflectances from the output unit 103 as the multi-angular reflectance property of the surface of the object 201. The two-dimensional distributions of reflectances corresponding to a plurality of declination angles represent the multi-angular reflectance property of the surface of the object 201.

FIG. 3B is a graph showing the relationship between the declination angle θ and the reflectance for a given measurement point. More specifically, the reflectance of a measurement point present at a position ($i_1$, $j_1$) is plotted along the ordinate from the N+1 two-dimensional distribution data of reflectances shown in FIG. 3A, and a corresponding declination angle θ is plotted along the abscissa, thereby representing the multi-angular reflectance property of the measurement position ($i_1$, $j_1$). A reflectance characteristic 301 with respect to the N+1 declination angles θ is interpolated or extrapolated using a known method such as linear interpolation, spline interpolation, or function approximation. As a result, a reflectance with respect to an arbitrary angle θ can be acquired. A range 302 represents a region having a small declination angle θ, that is, a neighboring region in the specular reflection direction at a measurement point. Note that the neighborhood of the specular reflection direction in this embodiment represents a direction within a predetermined angle in the specular reflection direction at a measurement point. The neighborhood of the specular reflection direction will be referred to as "specular neighborhood".

As described above, the reflectance of an object generally high in image clarity, such as a metal, greatly changes in the specular neighborhood. It is therefore necessary to change the declination angle θ more finely in the specular neighborhood region 302 than in other regions, and measure the reflectance in detail. A method of acquiring a reflectance R in the specular neighborhood by, for example, adjusting the tilt of the stage 111 without adjusting the declination angle θ will be explained below.

[Optical Arrangement]

Figure 4:
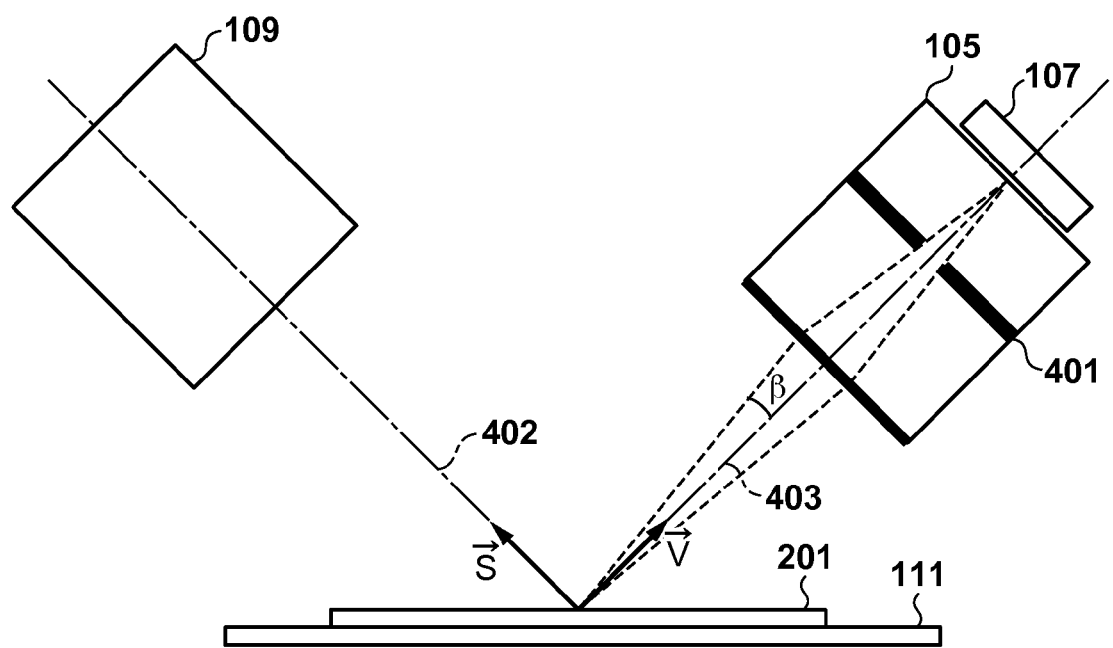
FIG. 4 is a view showing the optical arrangement of the respective units of the measurement apparatus.

The optical arrangement of respective units in the measurement apparatus according to this embodiment will be described with reference to FIG. 4. FIG. 4 is a view showing an example of the physical arrangement of the lens unit 105, sensor unit 107, illuminant unit 109, and stage 111. The diaphragm 401 incorporated in the lens unit 105 has an aperture of a circular shape or the like. The aperture size can be adjusted by moving the aperture blades or the like, and the lens unit controller 104 adjusts the aperture size. Note that the present invention does not limit the aperture shape and the physical adjustment method of the aperture size.

In this embodiment, the diaphragm 401 is disposed near the focus of the lens unit 105 so as to be telecentric in the space of an object to be measured. With the object-space telecentric characteristic, rays to be condensed by the lens unit 105 are limited to rays parallel to the optical axis, so the declination angle θ is kept constant at the full angle of view in capturing by the sensor unit 107. The parallelism between rays to be condensed by the lens unit 105 and the optical axis changes depending on the aperture size of the diaphragm 401. As the aperture is smaller, only more parallel rays are selected. As the aperture is larger, more non-parallel rays are mixed. By utilizing this fact, the reflectance in the specular neighborhood is acquired in the present invention. Note that the declination angle θ is not kept constant at the full angle of view in a general lens for capturing, but the direction of incident light can be restricted by the aperture size, and thus the general lens can be used as the lens unit 105 in the present invention.

An optical axis 402 is the optical axis of light emitted from the illuminant unit 109 to the object 201, and an optical axis 403 is the optical axis of the lens unit 105. The illuminant unit 109 and the lens unit 105 are disposed so that the optical axis 402 and the light source vector $\vec{S}$ become parallel to each other, and the optical axis 403 and the line-of-sight vector $\vec{V}$ become parallel to each other. The object 201 is placed on the stage 111, and the tilt of the stage 111 is adjusted so that the declination angle θ takes a predetermined value. An aperture angle β indicates the angle of a ray that is included in rays passing through the lens unit 105 and is not parallel to the optical axis 403. The aperture angle β is adjusted by the aperture size (aperture diameter φ), as described above. Note that the aperture angle β can be calculated based on the aperture diameter φ by:

$$\beta = \sin^{-1} \phi / 2D \qquad (3)$$

where D is the distance (to be referred to as a "capturing distance" hereinafter) on the optical axis 403 from the principal point of the lens unit 105 to the object 201.

In this embodiment, the aperture angle β is controlled by changing the aperture diameter φ by the lens unit controller 104.

[Arrangement of Measurement Processing]

Figure 14:
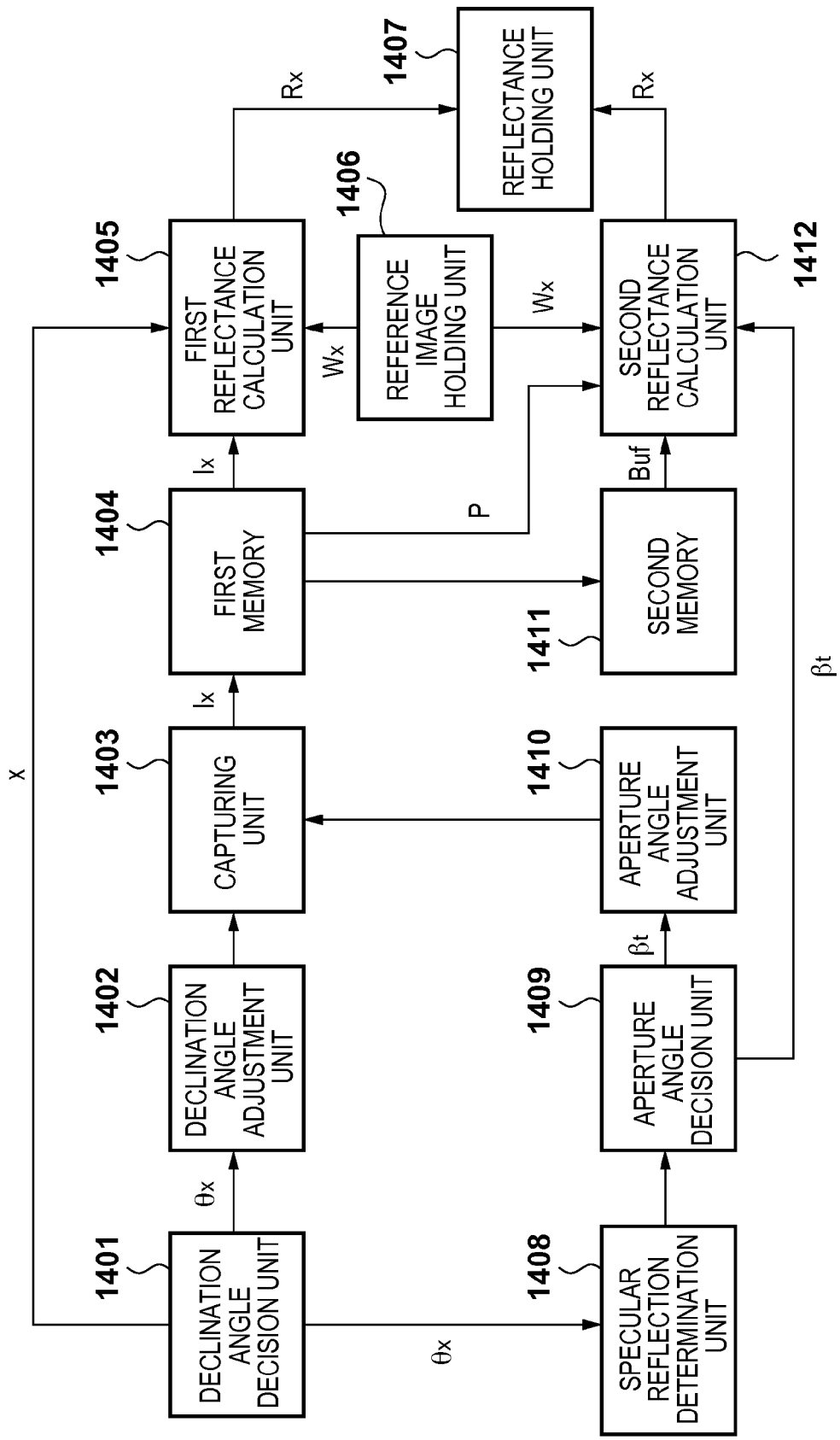
FIG. 14 is a block diagram showing the processing arrangement of the measurement apparatus according to the first embodiment.

FIG. 14 is a block diagram showing the processing arrangement of the measurement apparatus according to this embodiment. As described above, the processing arrangement shown in FIG. 14 is implemented by executing the measurement program by the CPU 112 of the measurement controller 101.

In FIG. 14, a declination angle decision unit 1401 decides the declination angle θ based on a preset declination angle order. A declination angle adjustment unit 1402 adjusts the tilt of the stage 111 and the like using the stage controller 110 so that geometric conditions in measurement match the declination angle θ decided by the declination angle decision unit 1401. By the tilt control of the stage 111, the declination angle θ can be changed at, for example, a constant step.

A capturing unit 1403 acquires image data using the sensor unit 107. The image data acquired by the capturing unit 1403 is stored in a first memory 1404 serving as a buffer allocated to the RAM 113 or the like.

A first reflectance calculation unit 1405 calculates the two-dimensional distribution of reflectances with respect to the declination angle θ based on image data stored in the first memory 1404, and reference image data held in a reference image holding unit 1406 allocated to the storage unit 117 or the like. The two-dimensional distribution of reflectances calculated by the first reflectance calculation unit 1405 is stored in a reflectance holding unit 1407 allocated to the storage unit 117 or the like.

A specular reflection determination unit 1408 determines whether the declination angle θ decided by the declination angle decision unit 1401 matches geometric conditions for measuring specular reflection of the object 201, that is, whether the declination angle θ is 0. When the specular reflection determination unit 1408 determines that the declination angle θ is 0, an aperture angle decision unit 1409 decides the aperture angle β of the lens unit 105 based on a preset aperture angle order.

An aperture angle adjustment unit 1410 calculates the aperture diameter φ from the relationship given by the above-described equation (3) so as to obtain the aperture angle β decided by the aperture angle decision unit 1409, and sends a command to the lens unit controller 104 so as to obtain the calculated aperture diameter φ. By performing aperture angle control in this manner, fine declination angle adjustment becomes possible. In the specular neighborhood, the declination angle can be changed at a step smaller than the change step of the declination angle by tilt control of the stage 111. When the aperture angle adjustment unit 1410 changes the aperture angle β of the lens unit 105, the capturing unit 1403 performs capturing, and image data is stored in the first memory 1404.

If necessary, image data stored in the first memory 1404 is copied to a second memory 1411. A second reflectance calculation unit 1412 calculates the declination angle θ from the aperture angle β. From image data stored in the first and second memories 1404 and 1411, and reference image data held in the reference image holding unit 1406, the second reflectance calculation unit 1412 calculates the two-dimensional distribution of reflectances (reflectances in the specular neighborhood) with respect to the calculated declination angle θ. The two-dimensional distribution of reflectances calculated by the second reflectance calculation unit 1412 is stored in the reflectance holding unit 1407.

[Multi-Angular Property Measurement Processing]

Figure 5:
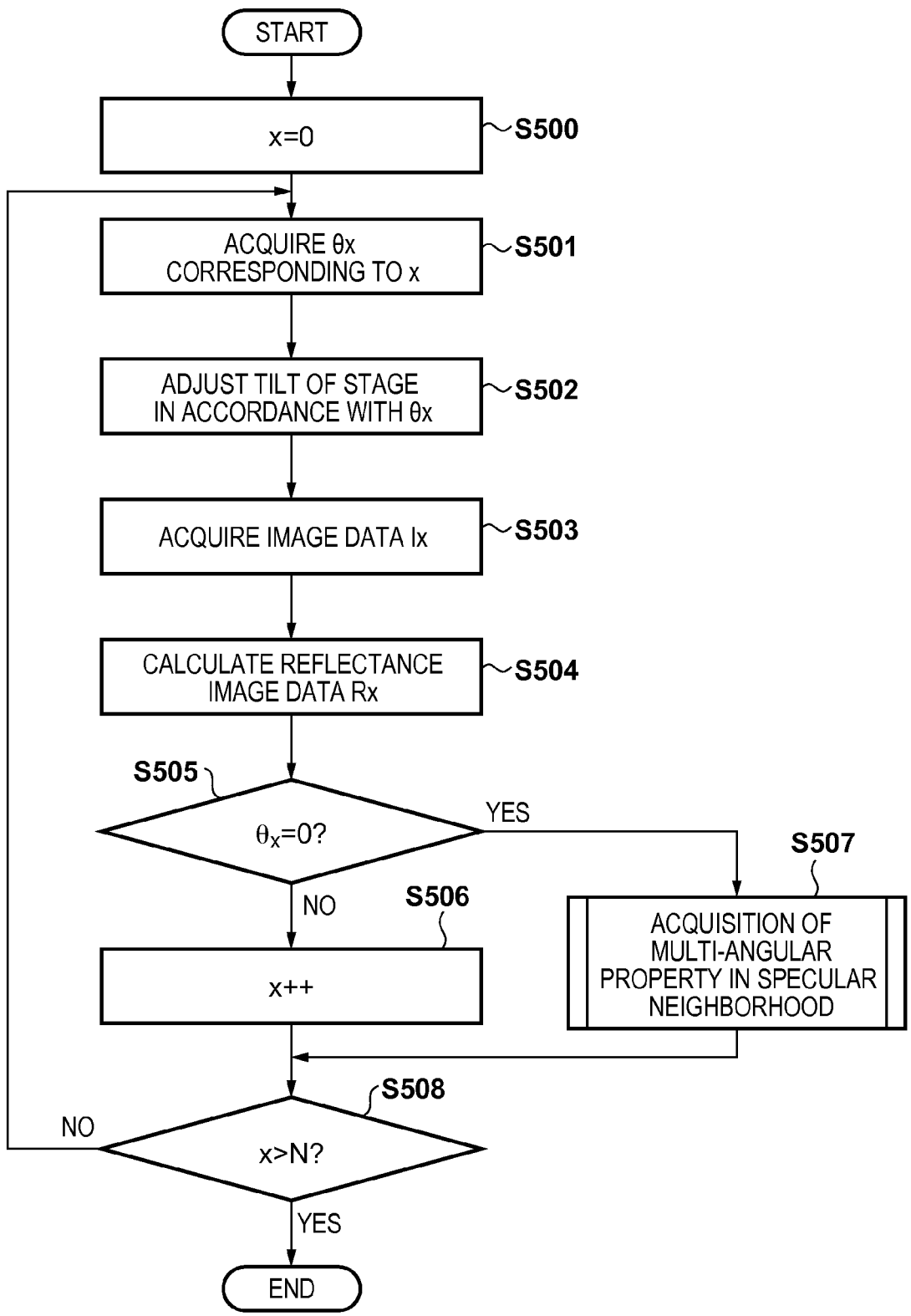
FIG. 5 is a flowchart showing multi-angular property measurement processing.

FIG. 5 is a flowchart showing multi-angular property measurement processing to be executed in the measurement apparatus according to this embodiment. The sequence of multi-angular property measurement processing in the measurement apparatus according to this embodiment, and the detailed operations of the respective units shown in FIG. 14 will be explained with reference to FIG. 5.

First, a variable x representing the index number of each two-dimensional distribution data shown in FIG. 3A is initialized to 0 (S500). Then, the declination angle decision unit 1401 acquires a declination angle θx that corresponds to the variable x and is uniquely decided in advance (S501). The declination angle adjustment unit 1402 adjusts the tilt of the stage 111 in accordance with the declination angle θx (S502). The capturing unit 1403 controls the sensor unit 107 to perform capturing, acquire image data Ix, and store the image data Ix in the first memory 1404 (S503).

The first reflectance calculation unit 1405 calculates reflectance image data Rx from the image data Ix, and stores the reflectance image data Rx in the reflectance holding unit 1407 (S504). The reflectance image data Rx calculated in step S504 is data corresponding to the declination angle θx implemented by tilt control of the stage 111, and is calculated by:

$$Rx(i,j)=Ix(i,j)/Wx(i,j) \quad (4)$$

where (i, j) is the pixel position (measurement point) of image data,

Ix(i, j) is the pixel value of the image data Ix at the position (i, j), and

Wx(i, j) is the value representing the intensity of incident light at the position (i, j).

The intensity Wx(i, j) of incident light is a value measured in advance, and a value measured for each declination angle θx is held in the reference image holding unit 1406. For example, the intensity Wx(i, j) of incident light at the angle θx can be acquired by placing a standard diffuse reflection plate instead of the object 201, performing capturing by the sensor unit 107 under the condition of the declination angle θx, and multiplying the obtained image data by the circular constant π. It is also possible to capture a highly smooth glass or the like as a reference plate, and use the pixel value of the image data directly as the intensity Wx(i, j) of incident light. By measuring the intensity Wx(i, j) of incident light for each declination angle θx and each measurement point (pixel), correction (shading correction) of unevenness of illuminance of the illuminant can be performed simultaneously. When it is assumed that no unevenness of illuminance of the illuminant would occur and uniform illumination of the object 201 is possible, the intensity of incident light may take a constant value W regardless of the measurement point (pixel) and the declination angle θx.

Referring back to FIG. 5, the specular reflection determination unit 1408 determines whether the declination angle θx is 0° (S505). If θx≠0, the specular reflection determination unit 1408 determines that this measurement is measurement of a region other than the specular neighborhood, and the variable x is incremented (S506). It is then determined whether the variable x is larger than a predetermined number N (S507). If x>N, it is determined that all N+1 measurement operations have ended, and the process ends. If x≤N, the process returns to step S501 in order to acquire two-dimensional distribution data under the next declination angle condition.

If θx=0 in step S505, the specular reflection determination unit 1408 determines that this measurement is measurement of the specular neighborhood, and the process advances to step S507. In step S507, a more detailed property in the specular neighborhood is acquired. The processing in step S507 is processing of performing aperture angle control in the specular neighborhood region 302 shown in FIG. 3B and acquiring a reflectance property at a smaller declination angle step. After that, the process advances to step S508 to determine whether all measurement operations have ended.

Multi-Angular Property Acquisition Processing in Specular Neighborhood

Figure 6:
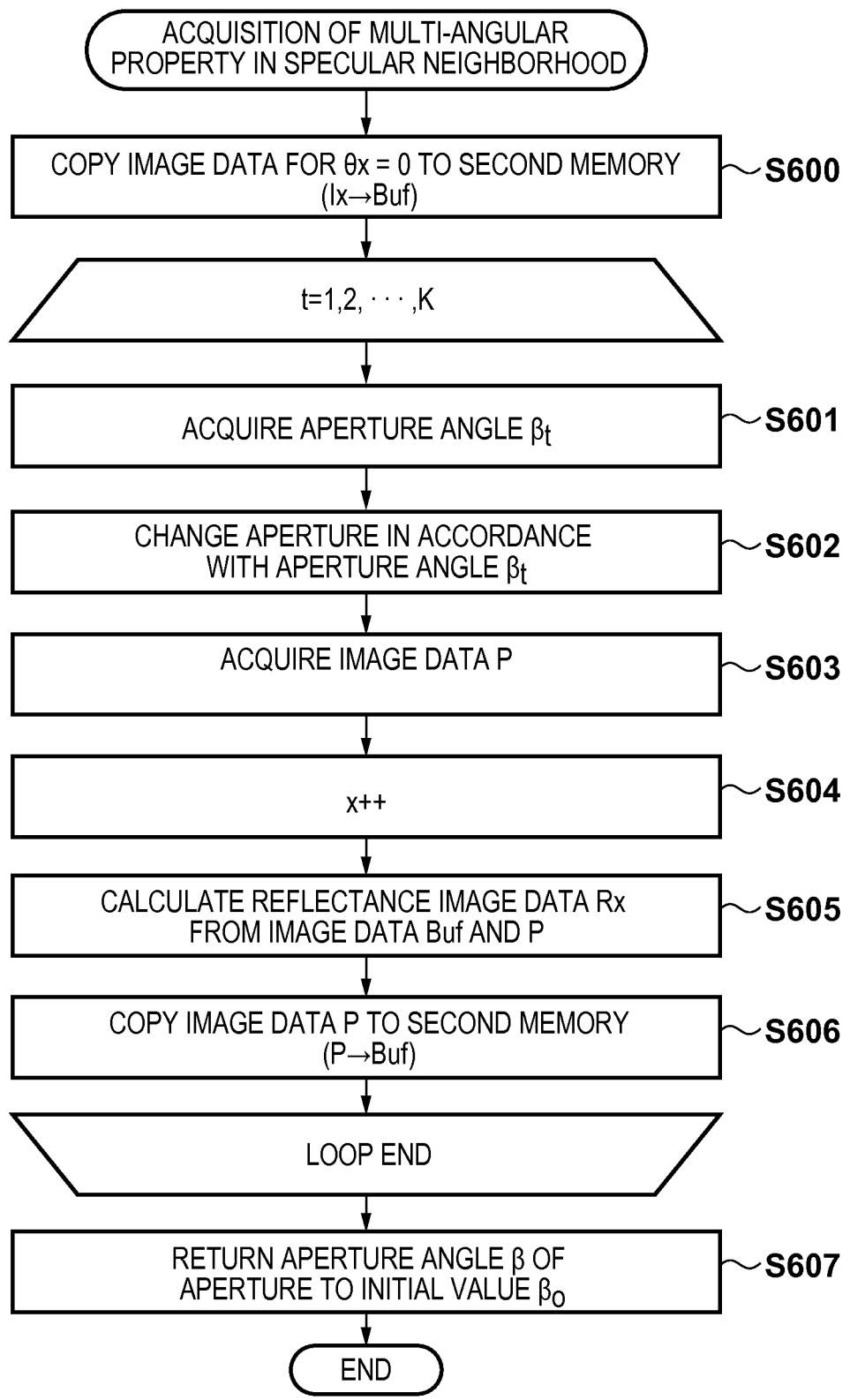
FIG. 6 is a flowchart showing multi-angular property acquisition processing for the specular neighborhood.

The multi-angular property acquisition processing (S507) in the specular neighborhood will be explained in detail with reference to the flowchart of FIG. 6. First, image data for θx=0 that has already been obtained by capturing in step S503 and stored in the first memory 1404 is copied to the second memory 1411 (S600). The copied image data is represented by "Buf". Processing in steps S601 to S606 is repeated K times from a variable t=1 to t=K.

Then, the aperture angle decision unit 1409 acquires a predetermined aperture angle $β_t$ corresponding to the value of the variable t (S601). The aperture angle adjustment unit 1410 changes the aperture diameter φ of the diaphragm 401 in accordance with the aperture angle $β_t$ (S602). The capturing unit 1403 performs capturing, and stores newly acquired image data in the first memory 1404 (S603). The newly acquired image data is represented by "P".

The variable x representing the index number of two-dimensional distribution data is incremented (S604). Then, the second reflectance calculation unit 1412 calculates reflectance image data Rx from the image data Buf stored in the second memory 1411 and the image data P stored in the first memory 1404:

$$Rx(i,j)=\{(\sin β_0)^2/Wx(i,j)\} \cdot \{P(i,j)-Buf(i,j)\}/\{(\sin β_{t-1})^2-(\sin β_t)^2\} \quad (5)$$

where P(i, j) is the pixel value at a position (i, j) in the image data P,

Buf(i, j) is the pixel value at the position (i, j) in the image data Buf, $β_{t-1}$ is the aperture angle when the image data P was obtained by capturing, $β_t$ is the aperture angle when the image data Buf was obtained by capturing, and $β_0$ is the aperture angle at the time of capturing for acquiring Wx (this aperture angle is the same as an aperture angle when image data for θx=0 was obtained by capturing).

In equation (5), the increment P(i, j)−Buf(i, j) of the pixel value when the aperture angle was changed from $\beta_t$ to $\beta_{t-1}$ is divided by the change amount $(\sin \beta_{t-1})^2 - (\sin \beta_t)^2$ of a solid angle. As a result, a value equivalent to a luminance value per unit solid angle between $\beta_{t-1}$ to $\beta_t$ is calculated. By dividing Wx(i, j) by $(\sin \beta_0)^2$, a value equivalent to the intensity of incident light per unit solid angle is obtained. In equation (5), a value equivalent to the reflectance is calculated by multiplying a reciprocal $(\sin \beta_0)^2/Wx(i, j)$ of the intensity of incident light per unit solid angle. Note that the declination angle θx with respect to the reflectance image data Rx at this time can be calculated as the average of $\beta_{t-1}$ and $\beta_t$:

$$\theta x = (\beta_{t-1} - \beta_t)/2 \qquad (6)$$

Referring back to FIG. 6, the image data P in the first memory 1404 is copied to the second memory 1411 in order to repeat the measurement processing (S606). The measurement processing in steps S601 to S606 is repeated K times in accordance with K preset aperture angles $\beta_t$. In this way, the aperture diameter φ is changed to set a different aperture angle $\beta_t$ in every repetition, and the reflectance image data Rx is calculated in accordance with equation (5). In this repetition, it is desirable to change the aperture diameter φ in the ascending order or descending order, in other words, change the aperture to gradually increase or gradually decrease. However, the present invention is not limited to this example.

After the end of measurement at all aperture angles $\beta_t$ each corresponding to the variable t, the aperture angle adjustment unit 1410 returns the aperture angle β of the aperture of the diaphragm 401 to the initial value $\beta_0$ so that the aperture angle β in next capturing (S503) becomes the initial value $\beta_0$ (S607). Thereafter, the multi-angular property acquisition processing in the specular neighborhood ends.

Figure 7:
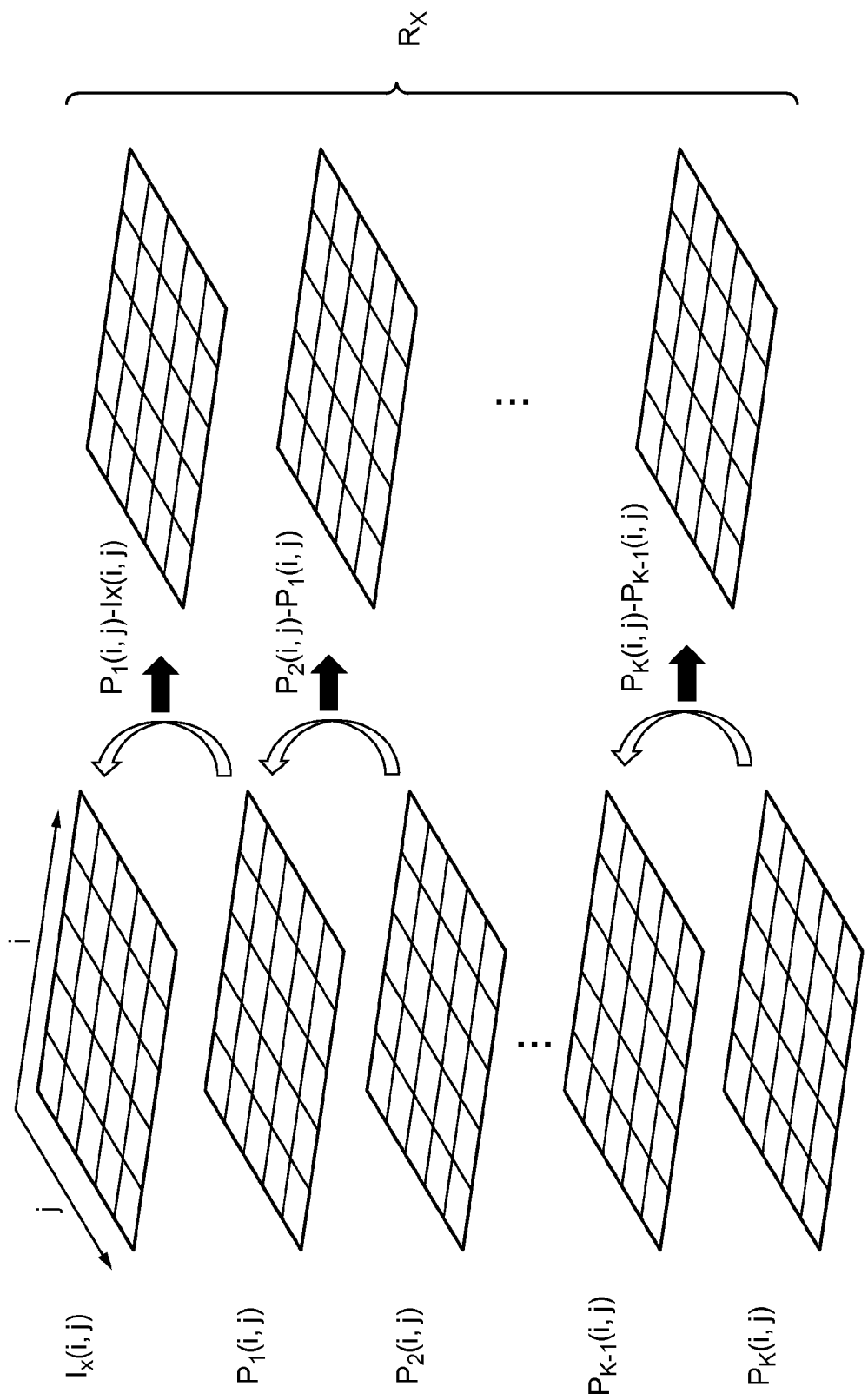
FIG. 7 is a view for explaining reflectance acquisition processing for the specular neighborhood.

The reflectance acquisition processing in the specular neighborhood in steps S601 to S606 will be described with reference to FIG. 7. The left side of FIG. 7 shows the image data P acquired in step S603 by K times of repetition. Note that the suffix of P represents the number t of times of repetition. The top image data Ix is image data at the declination angle θx=0 and the aperture angle $\beta_0$ that was obtained by capturing in step S503. In other words, a plurality of image data on the left side are image data obtained by capturing at the common declination angle θx=0 and different aperture angles β. The right side of FIG. 7 schematically shows that the reflectance image data Rx is calculated as a difference between vertically adjacent image data shown on the left side.

Figure 8:
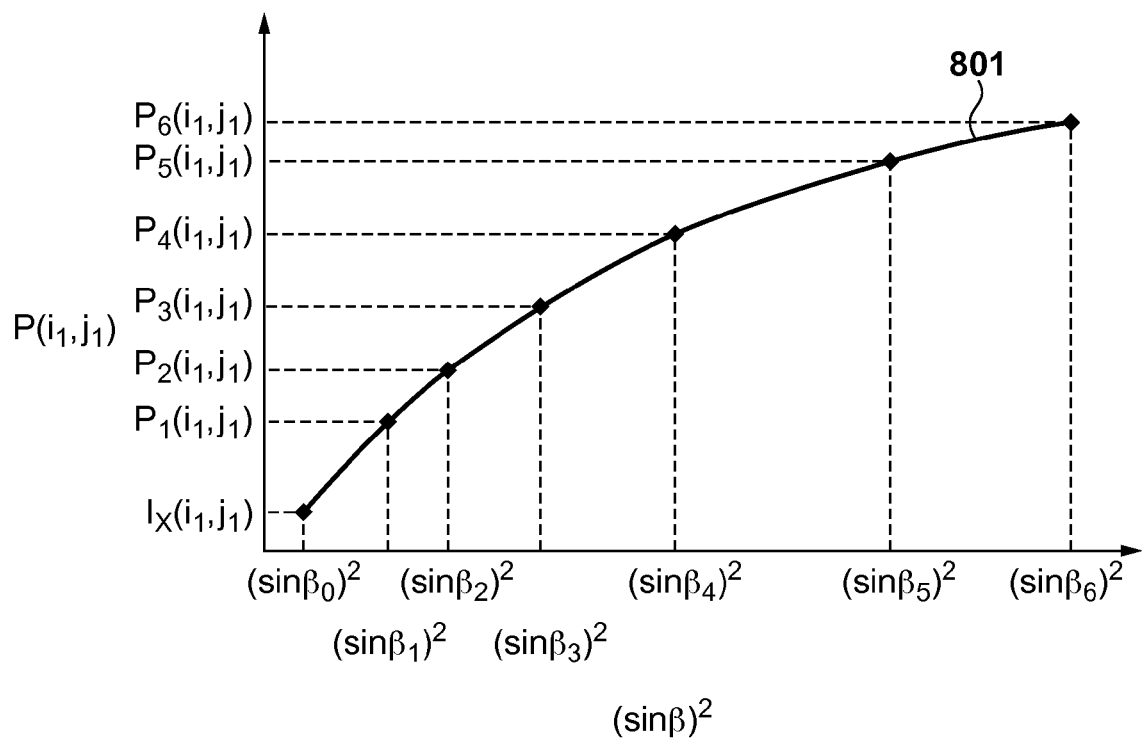
FIG. 8 is a graph showing an aperture angle-to-pixel value characteristic.

FIG. 8 shows a pixel value-to-aperture angle characteristic 801 for a given measurement point $(i_1, j_1)$ when the pixel values of all image data shown on the left side of FIG. 7 are plotted along the ordinate and the squares of the sines of the corresponding aperture angles β are plotted along the abscissa. In FIG. 8, it is assumed that the aperture angle $\beta_t$ increases as the measurement processing in steps S601 to S606 is repeated. In the multi-angular property acquisition processing (S507) for the specular neighborhood, the characteristic 801 shown in FIG. 8 is differentiated to estimate a pixel value per unit solid angle and calculate a reflectance property.

Figure 9:
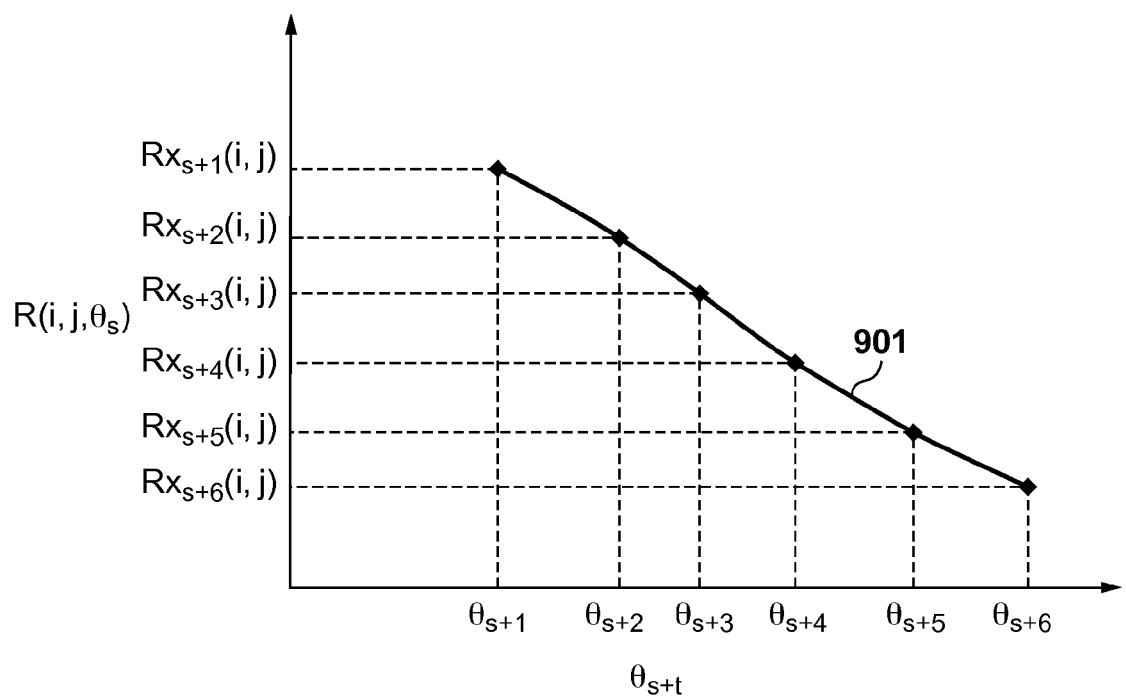
FIG. 9 is a graph showing a multi-angular reflectance property in the specular neighborhood.

FIG. 9 shows an example of the relationship (a multi-angular reflectance property 901) between the declination angle θ and the reflectance, which has been acquired in the multi-angular property acquisition processing (S507) for the specular neighborhood. In FIG. 9, $x_s$ corresponds to an index number at θx=0, and $x_{s+t}$ represents the measurement time in the multi-angular property acquisition processing for the specular neighborhood.

The measurement apparatus according to this embodiment outputs N+1 reflectance image data Rx measured in the above-described manner. The N+1 reflectance image data Rx represent the multi-angular reflectance property of the object 201 to be measured.

As described above, the multi-angular property of the reflectance in the specular neighborhood is measured by changing the aperture angle β of the lens unit 105 without changing geometric conditions such as the irradiation direction of light and the capturing direction. The multi-angular property of the reflectance in the specular neighborhood can be measured without using a device such as a high-accuracy, high-resolution multi-angle stage capable of finely adjusting the declination angle β. Hence, the reflectance in the specular neighborhood can be acquired at high accuracy even in a low-cost apparatus in which the mechanical accuracy for adjusting the declination angle θ is relatively low. Since the declination angle θ need not be changed mechanically in the specular neighborhood, a reflectance with respect to the necessary declination angle θ can be measured in a shorter time.

In the above example, the reflectance is calculated based on equation (4) or (5). However, the present invention is not limited to this example, and may adopt another method as long as a value equivalent to the reflectance is obtained or a value can be easily converted into a reflectance by numerical calculation.

The change step (interval of the declination angle θ decided by the declination angle decision unit 1401) of the declination angle θ when acquiring the reflectance of a region other than the specular neighborhood region 302 in FIG. 3B suffices to be small enough to acquire the diffuse component of reflected light. The interval of the declination angle θ can be set to be, for example, about 10° though it changes depending on the material of the object 201 to be measured. The change step (interval of the aperture angle β decided by the aperture angle decision unit 1409) of the aperture angle β in the specular neighborhood region 302 requires a relatively small interval though it changes depending on the material of the object 201 to be measured, because of the premise on specular reflection. For example, the interval of the aperture angle β is preferably equal to or smaller than 0.5°.

Second Embodiment

The second embodiment according to the present invention will be described below. The first embodiment has described a method of controlling the diaphragm 401 of the lens unit 105 in order to change the aperture angle β serving as a geometric condition of rays passing through the lens unit 105. In the second embodiment, the aperture angle β is changed by changing even the distance between a lens unit 105 and an object 201 to be measured, in addition to a diaphragm 401 of the lens unit 105. Note that the arrangement of a measurement apparatus and a basic processing sequence in the second embodiment are the same as those in the first embodiment, thus a description thereof will not be repeated, and only a difference from the first embodiment will be explained below.

[Lens Unit Controller]

Figure 15:
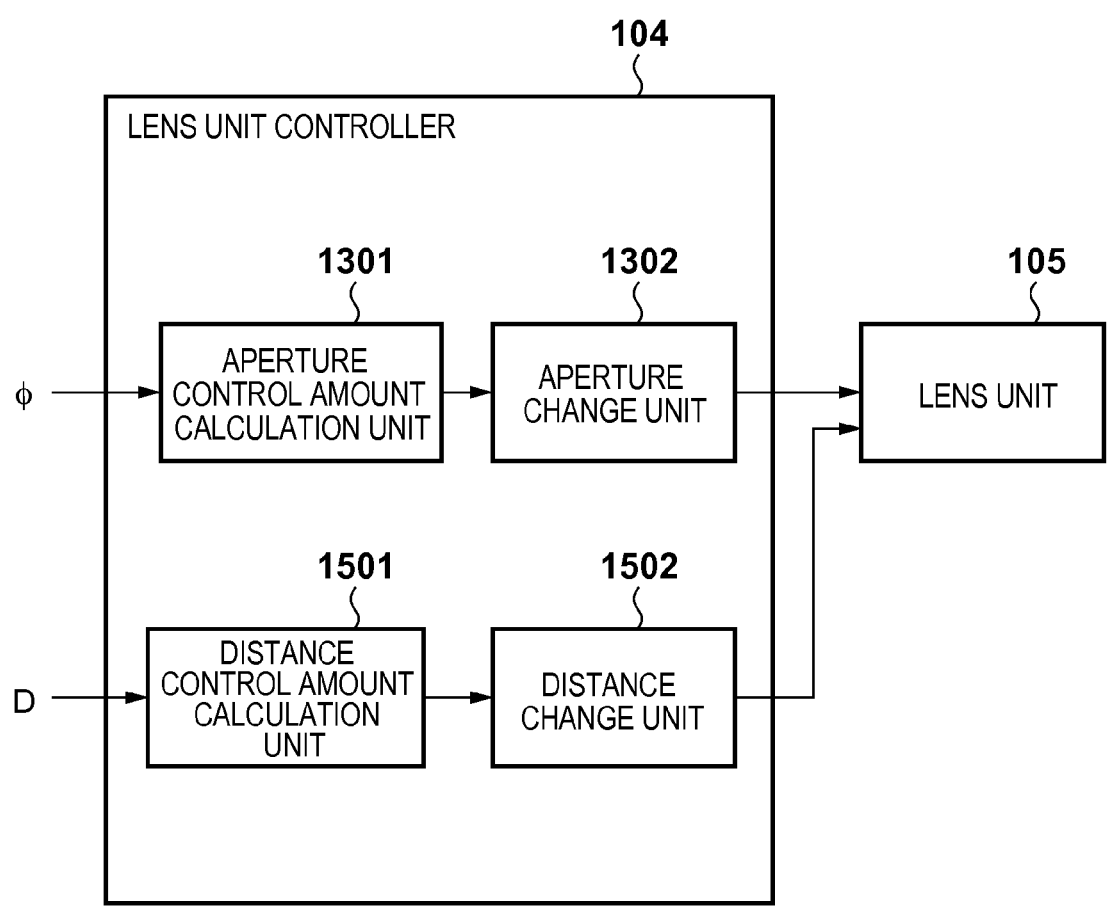
FIG. 15 is a block diagram showing the arrangement of a lens unit controller according to the second embodiment.

FIG. 15 is a block diagram showing the arrangement of a lens unit controller 104 according to the second embodiment. The lens unit controller 104 according to the second embodiment includes a distance control amount calculation unit 1501 and a distance change unit 1502, in addition to an aperture control amount calculation unit 1301 and an aperture change unit 1302 shown in FIG. 13. The distance control amount calculation unit 1501 calculates a control amount representing the amount of movement from the current position of the lens unit 105, in order to change the capturing distance of the lens unit 105 with respect to a capturing distance D input from a measurement controller 101. The distance change unit 1502 moves the lens unit 105 along an optical axis 403 by the control amount calculated by the distance control amount calculation unit 1501.

[Multi-Angular Property Acquisition Processing in Specular Neighborhood]

Multi-angular property measurement processing in the second embodiment complies with the flowchart shown in FIG. 5 except for details of multi-angular property acquisition processing (S507) for the specular neighborhood. Multi-angular property acquisition processing (S507) in the specular neighborhood according to the second embodiment will be explained with reference to the flowchart of FIG. 10. The multi-angular property acquisition processing in the specular neighborhood according to the second embodiment repeats the processing shown in FIG. 6 while changing the capturing distance D between the lens unit 105 and the object 201 to be measured. Note that the relationship between the aperture angle β, and the capturing distance D between the principal point of the lens unit 105 and the object 201 is the same as that described with reference to equation (3).

Figure 10:
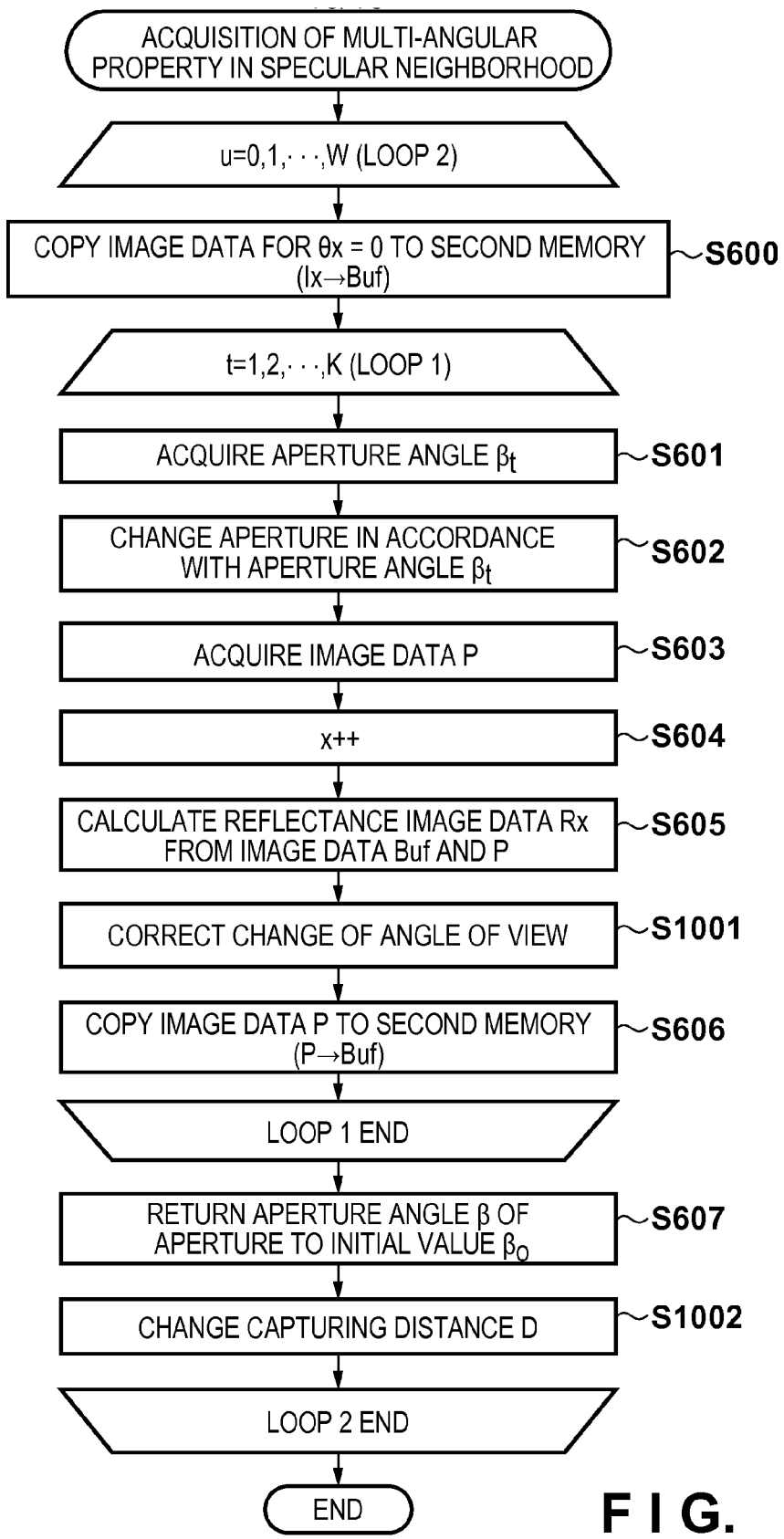
FIG. 10 is a flowchart showing multi-angular property acquisition processing in the specular neighborhood according to the second embodiment.

In FIG. 10, the repetition of processing in steps S601 to S606 that is repeated K times from a variable t=1 to t=K will be called "loop 1". The repetition of processing in steps S600 to S1002 that is repeated W times from a variable u=1 to u=W will be called "loop 2".

Final step S1002 in loop 2 is processing of changing the capturing distance D. The capturing distance D is changed by moving the lens unit 105 by a designated amount by the lens unit controller 104. At this time, even the positional relationship between a sensor unit 107 and the lens unit 105 is adjusted so that light reflected by the surface of the object 201 forms an image on the sensor unit 107. Note that the capturing distance D is set in advance in correspondence with the variable u.

Step S1001 included in loop 1 is processing of correcting a change of the angle of view arising from a change of the capturing distance D in step S1002. More specifically, an angle of view for a shortest capturing distance D is defined as a reference angle of view. A region matching the reference angle of view is extracted from reflectance image data Rx corresponding to a different capturing distance D. Then, resolution conversion is performed on reflectance image data of the extracted region so that the number of pixels of the region coincides with the number of pixels at the reference angle of view.

The aperture angle β can be adjusted at a smaller step by performing measurement in which the capturing distance D is changed in multi-angular property acquisition processing for the specular neighborhood. Therefore, the reflectance in the specular neighborhood can be acquired at higher accuracy.

In the second embodiment, the aperture angle β serving as a geometric condition of rays passing through the lens unit 105 is changed by controlling the aperture diameter ϕ and the capturing distance D. However, the aperture angle β can also be changed by controlling only the capturing distance D.

Third Embodiment

The third embodiment according to the present invention will be described below. In the third embodiment, higher-accuracy two-dimensional distribution data of reflectances can be acquired by capturing an image that is in focus at higher accuracy in the full angle of view.

[Optical Arrangement]

Figure 11:
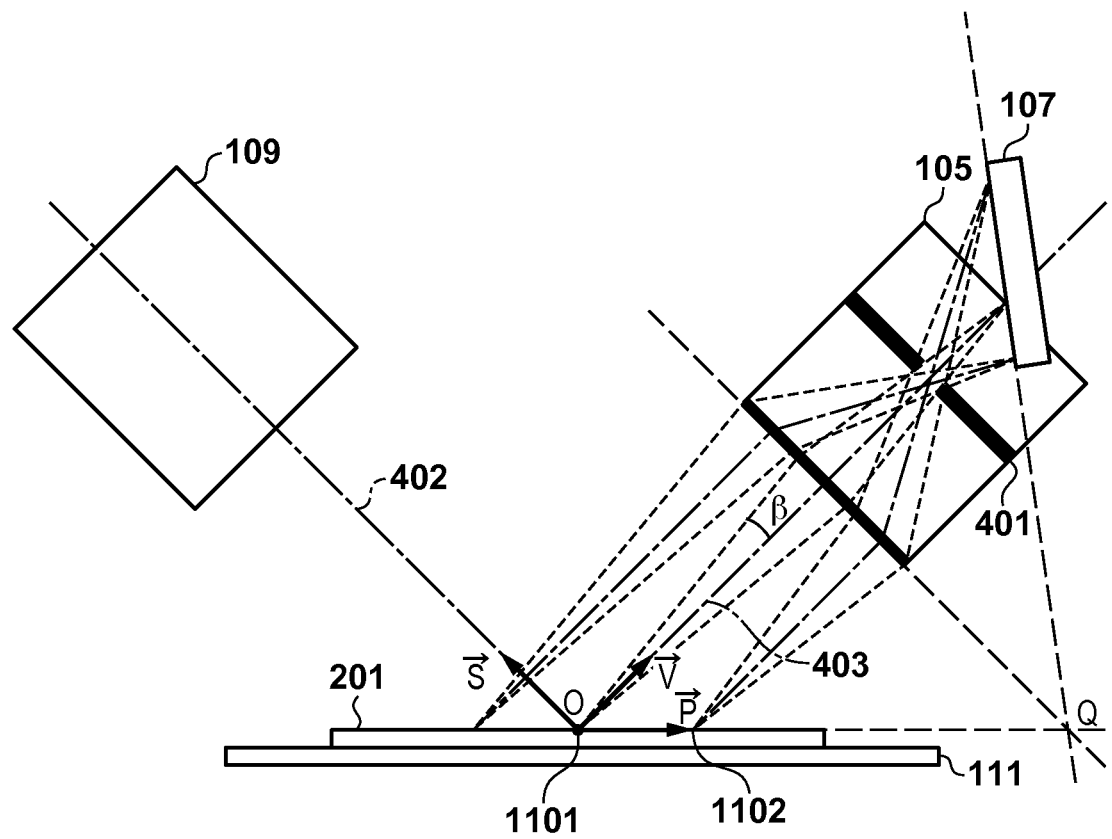
FIG. 11 is a view showing the optical arrangement of the respective units of a measurement apparatus according to the third embodiment.

FIG. 11 shows the optical arrangement of respective units in a measurement apparatus according to the third embodiment. As shown in FIG. 11, the optical arrangement according to the third embodiment is different from the optical arrangement shown in FIG. 4 in that a sensor unit 107 has a tilt with respect to a lens unit 105. By inclining the lens unit 105 in this manner, the focus on the surface of an object 201 to be measured can be adjusted at high accuracy. The tilt angle of the sensor unit 107 complies with a well-known Scheimpflug principle. Although a detailed description will be omitted, the entire surface of the object 201 is in focus by setting the light receiving surface of the sensor unit 107, the principal plane of the lens unit 105, and the surface of the object 201 to have a positional relationship in which their extended planes cross each other on a straight line Q.

[Multi-Angular Property Acquisition Processing in Specular Neighborhood]

Figure 12:
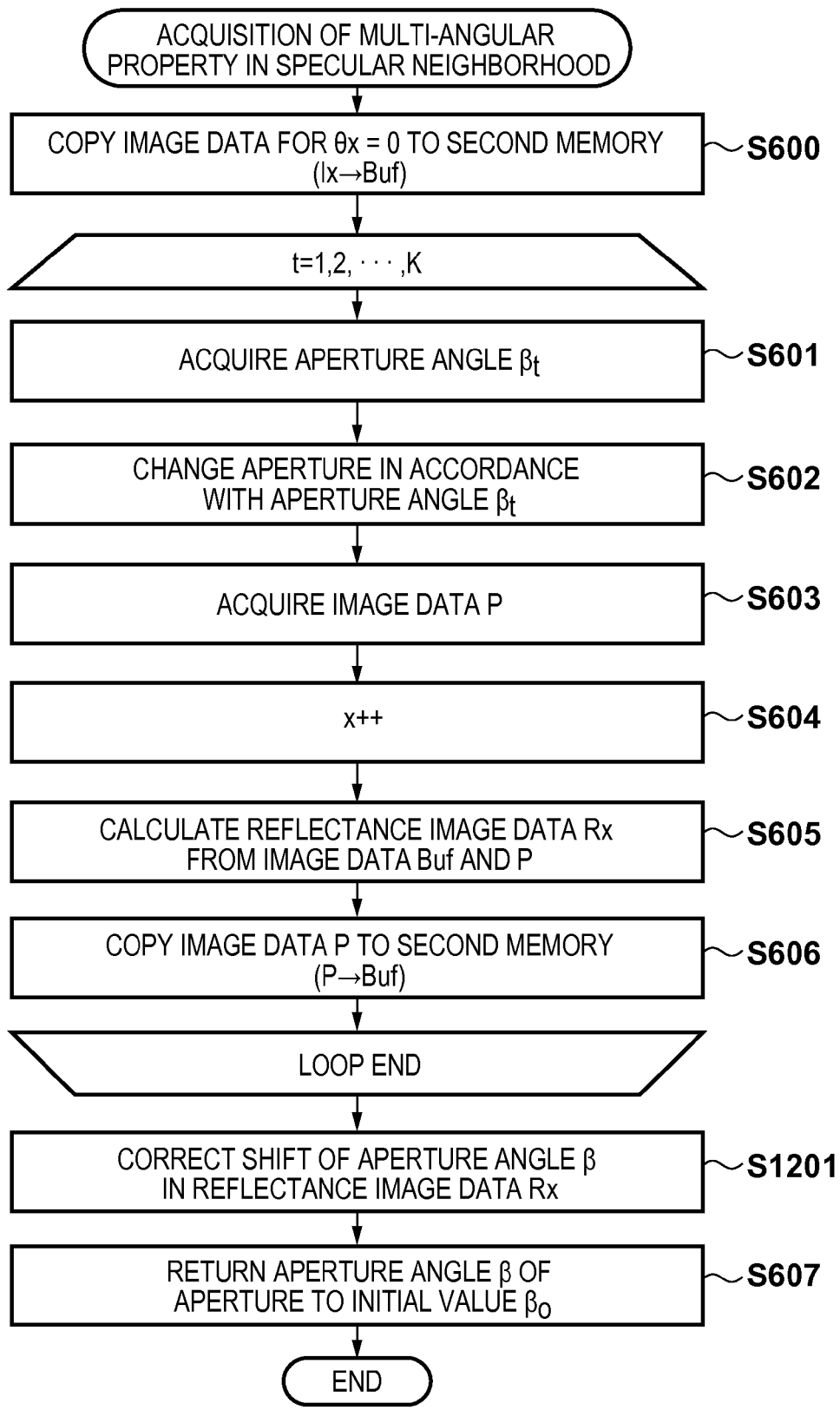
FIG. 12 is a flowchart showing multi-angular property acquisition processing in the specular neighborhood according to the third embodiment.
Figure 16:
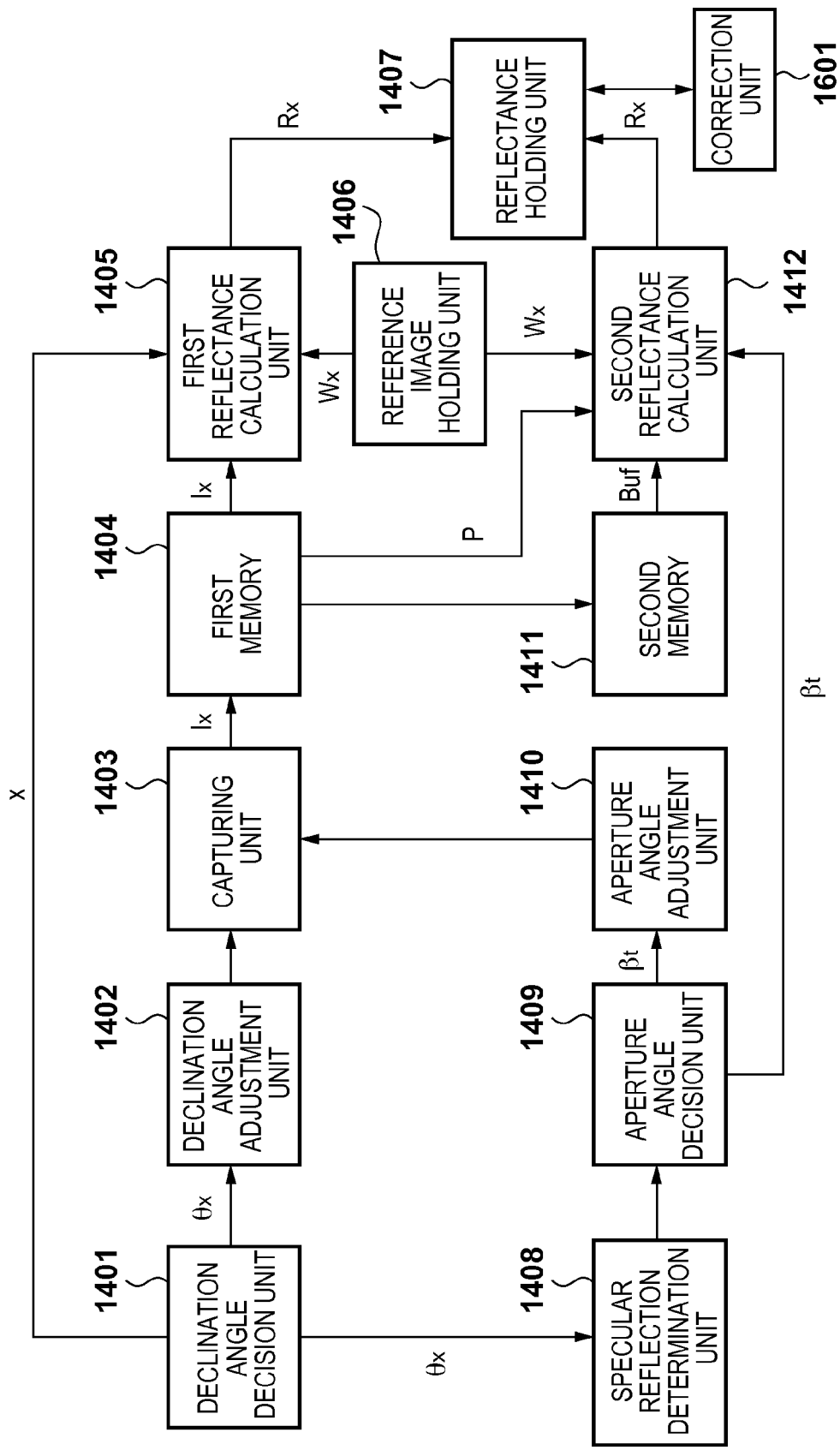
FIG. 16 is a block diagram showing the processing arrangement of the measurement apparatus according to the third embodiment.

Multi-angular property measurement processing in the third embodiment complies with the flowchart shown in FIG. 5 except for details of multi-angular property acquisition processing (S507) for the specular neighborhood. Multi-angular property acquisition processing (S507) in the specular neighborhood according to the third embodiment will be explained with reference to the flowchart of FIG. 12. The multi-angular property acquisition processing in the specular neighborhood according to the third embodiment is different in that processing (S1201) of correcting measured reflectance image data Rx is added to the processing shown in FIG. 6. FIG. 16 is a block diagram showing the processing arrangement of the measurement apparatus according to the third embodiment. This arrangement is different from the arrangement shown in FIG. 14 in that a correction unit 1601 is added. The correction unit 1601 corrects, in the reflectance image data Rx, a change of the aperture angle β depending on the pixel position of image data owing to the tilt of the sensor unit 107 (S1201).

The reason why the aperture angle β changes depending on the pixel position when the sensor unit 107 is tilted will be explained here. In FIG. 11, the point of intersection between an optical axis 403 of the lens unit 105 and the surface of the object 201 is defined as a reference point O. $\vec{P}$ represents a vector from the reference point O to an arbitrary point 1102 on the surface of the object 201, and $\vec{V}$ represents the line-of-sight vector of the reference point O. Then, a variation d between the distance between the reference point O and the lens unit 105, and the distance between the point 1102 and the lens unit 105 can be calculated by:

$$d = (\vec{V} \cdot \vec{P})/|\vec{V}| \quad (7)$$

From this, the aperture angle β with respect to the point 1102 can be calculated by:

$$\beta = \sin^{-1} \phi/2(D-d) \quad (8)$$

where ϕ is the aperture diameter of a diaphragm 401, and D is the distance from the principal point of the lens unit 105 to the reference point O.

As is apparent from equation (8), the aperture angle β differs between pixels in the third embodiment. In an acquired multi-angular reflectance property, for example, the multi-angular reflectance property in the specular neighborhood shown in FIG. 9, the declination angle θ along the abscissa shifts for every pixel. The correction unit 1601 corrects this shift. The correction unit 1601 holds in advance a plurality of representative declination angles θd common to all pixels, and performs correction on a multi-angular reflectance property corresponding to the representative declination angles θd. First, reflectances are acquired for the respective pixels of a plurality of reflectance image data Rx stored in a reflectance holding unit 1407. Then, reflectances corresponding to the representative declination angles θd are acquired for the respective pixels using linear interpolation, spline interpolation, or the like, and the reflectances of the respective pixels are replaced with the reflectances corresponding to the representative declination angles θd. As a result, a multi-angular reflectance property corresponding to the representative declination angles θd is obtained for all pixels.

In this fashion, image data in focus at higher accuracy with respect to the full angle of view can be obtained to acquire a higher-accuracy two-dimensional distribution of reflectances. Accordingly, a higher-accuracy multi-angular reflectance property including the specular neighborhood can be acquired.

Modification of Embodiments

Each embodiment described above has explained an example in which the half vector $\vec{H}$ between the line-of-sight vector $\vec{V}$ and the light source vector $\vec{S}$ is calculated, the angle θ between the half vector $\vec{H}$ and the normal vector $\vec{N}$ of an object to be measured is set as a declination angle, and a reflectance with respect to the declination angle θ is acquired. However, the present invention is not limited to this. For example, the present invention is also applicable to only the specular neighborhood in a measurement apparatus that acquires a reflectance with respect to the normal vector $\vec{N}$ and the light source vector $\vec{S}$.

Each embodiment is premised on that the lens unit 105 is focused on the surface of an object to be measured. However, the present invention is not limited to this, and the lens unit 105 may be focused on the exit plane of the illuminant unit 109. In this case, the resolution of the two-dimensional distribution decreases, but focus adjustment as described in the third embodiment becomes unnecessary and the same effects as those described above are obtained.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-049314 filed Mar. 12, 2014 which is hereby incorporated by reference herein in its entirety.

What is claimed is:

1. A measurement apparatus comprising:
   a sensor that photoelectrically converts received light to output image data;
   a lens that condenses light reflected by an object surface to be measured on the sensor;
   a lens control unit configured to control aperture angles of rays passing through the lens so that the aperture angles of the rays incident on the sensor are different;
   a measurement control unit configured to control the sensor and the lens control unit so as to acquire a multi-angular reflectance property in a neighborhood of a specular reflection direction of the object surface;
   a stage on which an object to be measured is placed; and
   a stage control unit configured to control a tilt of the stage,
   wherein the stage control unit changes the tilt of the stage in accordance with a declination angle instructed by the measurement control unit, and the sensor outputs image data corresponding to the declination angle,
   wherein the measurement control unit acquires a reflectance property of the object surface corresponding to the declination angle from the image data corresponding to the declination angle, and
   wherein the lens has object-space telecentricity, the sensor is an area sensor in which light receiving elements are arranged two-dimensionally, and the reflectance property represents a two-dimensional distribution of reflectances in the object surface.

2. The apparatus according to claim 1, wherein the lens control unit changes the aperture angles of the rays and the sensor outputs a plurality of image data corresponding to the aperture angles, based on instructions of the measurement control unit, and
   wherein the measurement control unit acquires the multi-angular reflectance property in the neighborhood of the specular reflection direction based on a correspondence of the aperture angles and the plurality of image data.

3. The apparatus according to claim 2, wherein the lens control unit controls an aperture diameter of a diaphragm of the lens to change the aperture angles.

4. The apparatus according to claim 2, wherein the lens control unit controls a distance between the lens unit and the object surface to change the aperture angles.

5. The apparatus according to claim 2, wherein the lens control unit controls an aperture diameter of a diaphragm of the lens and a distance between the lens and the object surface to change the aperture angles.

6. The apparatus according to claim 3, wherein the measurement control unit performs the instructions for changing the aperture angles in a predetermined step to acquire the multi-angular reflectance property in the neighborhood of the specular reflection direction.

7. The apparatus according to claim 1, wherein the declination angle is an angle formed by an intermediate vector and a normal vector of the object surface, and the intermediate vector indicates an intermediate direction of a direction of an illuminant from the object surface and a direction of observing the object surface.

8. The apparatus according to claim 1, wherein the measurement control unit performs the instruction for changing the declination angle in a predetermined step to acquire the multi-angular reflectance property of the object surface.

9. The apparatus according to claim 1, wherein, in a case where the declination angle becomes zero, the measurement control unit performs an instruction to the lens control unit for changing the aperture angles.

10. The apparatus according to claim 1, wherein a light receiving surface of the sensor is disposed to be inclined to a principal plane of the lens, and
wherein the measurement control unit comprises a correction unit configured to correct pixel values of the image data output from the sensor to values corresponding to predetermined declination angles.

11. The apparatus according to claim 10, wherein an extended surface of the light receiving surface, an extended surface of the principal plane, and an extended surface of the object surface intersect on a line.

12. The apparatus according to claim 1, further comprising an illuminant unit configured to irradiate parallel rays to the object surface.

13. A method of a measurement apparatus which includes (a) a sensor that photoelectrically converts received light to output image data, (b) a lens that condenses light reflected by an object surface to be measured on the sensor, (c) a lens control unit configured to control aperture angles of rays passing through the lens so that the aperture angles of the rays incident on the sensor are different, and (d) a stage on which an object to be measured is placed, the method comprising:
controlling the sensor and the lens control unit so as to acquire a multi-angular reflectance property in a neighborhood of a specular reflection direction of the object surface,
wherein a tilt of the stage is changed in accordance with a declination angle, the sensor outputs image data corresponding to the declination angle, a reflectance property of the object surface corresponding to the declination angle is acquired from the image data corresponding to the declination angle, the lens has object-space telecentricity, the sensor is an area sensor in which light receiving elements are arranged two-dimensionally, and the reflectance property represents two-dimensional distribution of reflectances in the object surface.

14. A non-transitory computer readable medium storing a computer-executable program for causing a computer to perform a method of a measurement apparatus which includes (a) a sensor that photoelectrically converts received light to output image data, (b) a lens that condenses light reflected by an object surface to be measured on the sensor, (c) a lens control unit configured to control aperture angles of rays passing through the lens so that the aperture angles of the rays incident on the sensor are different, and (d) a stage on which an object to be measured is placed, the method comprising:
controlling the sensor and the lens control unit so as to acquire a multi-angular reflectance property in a neighborhood of a specular reflection direction of the object surface,
wherein a tilt of the stage is changed in accordance with a declination angle, the sensor outputs image data corresponding to the declination angle, a reflectance property of the object surface corresponding to the declination angle is acquired from the image data corresponding to the declination angle, the lens has object-space telecentricity, the sensor is an area sensor in which light receiving elements are arranged two-dimensionally, and the reflectance property represents two-dimensional distribution of reflectances in the object surface.

* * * * *